United States Patent [19]

Williams et al.

[11] Patent Number: 4,996,997
[45] Date of Patent: *Mar. 5, 1991

[54] PERMANENT WAVING PROCESS AND COMPOSITIONS

[75] Inventors: Barry W. Williams, Chicago, Ill.; Pamela M. Daniels, Gary, Ind.

[73] Assignee: Amethyst Investment Group, Inc., Chicago, Ill.

[*] Notice: The portion of the term of this patent subsequent to Nov. 28, 2006 has been disclaimed.

[21] Appl. No.: 157,842

[22] Filed: Feb. 19, 1988

[51] Int. Cl.$^5$ ............................................. A45D 7/04
[52] U.S. Cl. ................................... 132/204; 132/209; 424/72
[58] Field of Search .................. 424/72; 132/202, 203, 132/204, 205, 207, 209, 210

[56] References Cited

U.S. PATENT DOCUMENTS

| 4,391,286 | 7/1983 | Hsiung et al. | 132/204 |
|---|---|---|---|
| 4,416,297 | 11/1983 | Wolfram et al. | 424/70 |
| 4,572,220 | 2/1986 | Hsiung et al. | 132/203 |
| 4,588,760 | 5/1986 | Jachowicz et al. | 524/12 |
| 4,602,648 | 7/1986 | Syed et al. | 132/204 |

FOREIGN PATENT DOCUMENTS

| 0257256 | 3/1988 | European Pat. Off. . |
| 2066310 | 7/1981 | United Kingdom . |
| 2068031 | 8/1981 | United Kingdom . |
| 2114616 | 8/1983 | United Kingdom . |

OTHER PUBLICATIONS

"Guar Gum and its Application", by R. J. Chudzikowski, Soc. Cosmet. Chem. 22, 43–60, (1971), Society of Cosmetic Chemist of Great Britian.
Celanese Corporation product bulletins Nos. 114, 38, 23, 122, CN 175, CN 176, CN 174, 117, 118, 123, 124, 180.
A product brochure from High-Tek Polymers Inc.

*Primary Examiner*—Cary E. Stone
*Assistant Examiner*—Adriene B. Lepiane
*Attorney, Agent, or Firm*—Allegretti & Witcoff, Ltd.

[57] ABSTRACT

An improved permanent waving process is disclosed. The improved waving process produces hair styles characterized as bouncier, more full bodied with an open/looser pattern of curls. Furthermore, the waving process of the invention provides for improved humectant properties that results in significantly less maintenance than is typically required when conventional waving processes are used. This waving process is a step-by-step procedure involving the addition of a rearranger, a wrapping lotion, and a neutralizer, in combination with intermittent rinsing. The improved quality and settability of the hair is believed to be attributable to a synergistic effect of an improved rearranging composition and an improved wrapping lotion. The rearranging composition comprises a homogenous mixture of a salt of thioglycolic acid and a homopolymer of methyacrylamidopropyltrimethyl ammonium chloride (MAPTAC). A preferred rearranging composition includes a weight ratio of ammonium thioglycolate to monoethanolamine thioglycolate of from about 4:6 to about 7:3 and between about 1.0 to about 3.0% by weight of a cationic homopolymer of MAPTAC. The rearranging composition should also be pH adjusted to between about 3.0 and about 10.5. The improved wrapping lotion composition comprises a homogenous mixture of a guar component and a salt of thiogycolic acid. A preferred wrapping lotion composition includes between about 0.2 and about 2.5% by weight of a nonionic hydroxypropylated guar and between about 0.3 and about 7.0% ammonium thiogycolate. The wrapping lotion composition should also be pH adjusted to between about 7.0 and about 10.5 and have a viscosity in the range from about 500 cps to about 12,000 cps.

14 Claims, No Drawings

PERMANENT WAVING PROCESS AND COMPOSITIONS

BACKGROUND OF THE INVENTION

A. Field of Invention

This invention relates broadly to an improved permanent hair waving or curling process and the composition used therein.

B. Prior Art

Among the components of hair is a proteinaceous material called "keratin". The hair's keratin is made up of long fibrous polypeptide chains which are bonded together with horizontal cross bonds of two forms: hydrogen bonds and cystine bonds, also sometimes referred to as disulfide bonds.

Cystine bonds play an essential role in determining the degree of curl in hair. Some researches in the field believe that straight or slightly wavy hair has relatively fewer cystine bonds and relies heavily upon hydrogen bonding to produce curl or waves in the hair and that very curly hair has a relatively larger amount of cystine bonds. Other researchers in the field believe that straight hair and curly hair may have the same number of cystine bonds, but that the cystine bonds present in straight hair tend to occur in a relatively straight alignment, whereas the cystine bonds present in curly hair tend to occur out of alignment. Regardless of which theory is accepted, while the hydrogen bonds can be broken merely by wetting the hair, such that straight or slightly wavy hair will lose virtually all body when wet, very curly hair maintains its body even when wet because the cystine bonds are relatively unaffected by water. Thus, very curly hair cannot be easily reset into new or different hair styles different from its natural state merely by wetting and shaping the hair.

Permanent hair waving is usually carried out by subjecting the hair to a strong reducing agent, such as hydroxide or, more commonly, materials containing a free "—SH" group or thiol. These "thiol" materials are also called mercaptans. In this treatment, the hair is saturated with the thiol agent, which then acts to break the disulfide bonds.

When a sufficient number of hair disulfide bonds have been broken, the hair is rinsed, removing the unreacted thiol waving agent and disulfide reaction product. The hair is then realigned, e.g., usually by winding on rollers, in order to physically align previously unpaired hair protein thiol groups, i.e., one-half of the cystine groups. The hair and rollers are then saturated with an oxidizing agent, or neutralizer, such as hydrogen peroxide or a bromate salt, to reform disulfide bonds between the newly paired hair protein thiols and to give the hair a configuration or wave. This general process may be used to either add curl or straighten the hair.

Salts of thioglycolic acid, such as ammonium thioglycolate, and thioglycolic acid esters, such as glycerol mono thioglycolate, are typically utilized as the thiol waving agent. Other thiol-containing reagents such as thiolactic acid, beta-mercaptopropionic acid, beta-mercaptobutyric acid, mercaptosuccinic acid and alike have been suggested in the art to be effective.

Prior art waving processes are plagued with the problem of either underwaving or overwaving (under or over processing) that occurs during waving on different parts of a single hair fiber or different areas of the hair mass due to the physical or chemical condition of the hair itself. For example, hair which has been waved, or bleached, or both is more porous than hair which has not undergone these chemical treatments, e.g., these portions of the hair fiber near the hair root which has grown out since the last bleaching or waving. Similarly, even hair having no previous history of bleaching or waving is more porous near the tip end than near the root end simply because hair near the tip has been brushed more, or has been subjected to more weathering.

As a consequence of these porosity differences, the hair tends to take up more waving agent in some areas and less waving agent in others. Over waving or processing tends to occur in the more porous portions of the hair while underwaving or processing tends to occur in less porous areas. These trends are exactly the inverse of what is desired since the hair which usually needs the waving treatment the most gets the least waving, and visa versa.

Many products today are directed to the special problems and needs of the Black ethnic market. People in the Black ethnic market have, for example, hair characterized by a relatively large number of cystine bonds and relatively high dryness. Conventional permanent waving products have particular limitations applied to this market. Typically, the products result in a hair style that is either very curly and quite greasy or relatively straight and stiff and very dry. These prior products are characterized by the need for frequent, heavy maintenance, e.g., the consumer's application of activators and moisturizers on a daily basis or more than daily basis. None of the prior art compounds are able to produce a Black ethnic hairstyle characterized by thick, full-bodied hair fibers which form loose bouncy curls having good moisture retention.

Another problem that occurs during the hair disulfide bond breaking process is skin irritation caused by the thiol-containing agents. Irritation occurs usually because beauticians frequently use their bare fingers for the wrapping process.

U.S. Pat. No. 4,391,286 (Hsiung et al.) and related U.S. Pat. No. 4,572,220 (Hsiung et al.) both disclose hair conditioning formulations that claim to overcome some of the problems just described. The '286 patent teaches a composition of water having dissolved therein a quaternary nitrogen containing polymer and a water-soluble, disulfide-containing polycarboxylic acid or salt. The '220 patent teaches the same composition as the '286 patent with the addition of a thiol-containing waving agent. The preferred disulfide-containing polycarboxylic acids are formed by the oxidation of two molecules of mercapto-monocarboxylic acid. Examples of these compounds include dithiodiglycolic acid, three-dithiodipropionic acid, cystine, dithiodilactic acid, dithiodisuccinic acid and the like. The preferred quaternary nitrogen containing polymer is a cationic guar where a chloride anion is usually associated with the polymer. The cationic guar is distinguished from other forms or derivatives of guar gum, such as nonionic guar which does not contain quaternary nitrogen compounds. Both formulations disclosed in these two patents are specifically designed and recommended for use on the hair after shampooing and prior to a waving process (i.e., pre-wrap solutions).

Another hair conditioning formulation is disclosed in U.S. Pat. No. 4,588,760 (Jachowicz et al.). This formulation for decreasing hair hygroscopicity and improving settability comprises an aqueous solution of heximinium salt and resorcinol. To facilitate application of this conditioning formulation, it is disclosed that a cosmetically acceptable thickener, such as guar gum, may be incorporated into the formulation.

All of the known waving processes and solutions associated therewith are limited in their flexibility to produce a looser, bouncier, curl while maintaining the moisture of the curls. The present invention provides an improved in hair waving process, eliminating many of the problems associated with prior art processes and solutions.

SUMMARY OF THE INVENTION

Thus, an object of the present invention is to provide an improved hair waving process and further to provide an improved wrapping lotion composition for use in a hair waving process.

It is an object of this invention to provide a permanent waving process and wrapping lotion that produces a softer, bouncier curl with an overall open/looser pattern and that requires less maintenance to maintain the integrity of the curl.

A further object of the invention is to provide for improvements in straightness and versatility without dry frizzing of the hair.

A further object is to provide for a reduction in overall processing time, less irritation, less odor, and a reduction in the danger of overprocessing.

A still further object is to provide a waving process that imports more body, sheen and manageability to the hair with improved curl retention.

Accordingly, in a broad embodiment, the present invention is a process of waving hair by applying to the hair a rearranging composition with chemical properties sufficient to change the cystine bonds in the hair keratin to lanthionine bonds. The rearranging composition comprises a homogenous mixture of a salt of thioglycolic acid and a homopolymer of methylacrylamidopropyltrimethyl ammonium chloride. After the rearranger has been left on the hair for a time to accomplish conversion of the bonds, the hair is rinsed to flush away a substantial portion of the rearranging composition.

A wrapping lotion composition is then applied to the hair. The wrapping lotion comprises a homogeneous mixture of a salt of thioglycolic acid and a guar component. The hair, with wrapping lotion applied is wrapped around a rod or roller to produce a desired curl pattern. The hair with wrapping lotion applied is left on the rods for a predetermined length of time, preferably about 5 to about 15 minutes, in order to set or lock in the desired curl pattern. The wrapped hair is rinsed to flush away only excess wrapping lotion composition.

After rinsing, a neutralizer composition is applied to the hair, still on the rods, to lock in the curl pattern. The neutralizer is left on the hair for a sufficient period of time to reestablish the cystine bonds, after which the neutralizer is flushed away by rinsing the hair.

The improved rearranger comprises a salt of thioglycolatic acid and between about 1.0 and about 3.0% by weight of a cationic homopolymer of methacrylamidopropyltrimethyl ammonium chloride. In preferred form the rearranger also includes between about 6.0 and about 10.0% by weight of ammonium thioglycolate, between about 3.0 and about 7.0% by weight of monoethanolamine thioglycolate. Also, in preferred form, the rearranger has a pH of between about 8.0 and about 10.5.

The improved wrapping lotion comprises between about 0.8 and about 2.5% by weight of a guar component, preferably nonionic guar gum and between about 0.3 and about 7.0% by weight of a salt of thioglycolic acid, preferably ammonium thioglycolate. In preferred form the wrapping lotion has a pH of between about 7.0 and about 10.5 and a viscosity of between about 1,800 to 2,200 cps.

These as well as other objects and embodiments will become apparent upon review of the more detailed description of the invention hereinafter set forth.

DETAILED DESCRIPTION OF THE INVENTION

The waving process of the instant invention is comprised of several steps, some of which involve the application of specific hair treatment formulations. As a first step, a rearranging composition is applied to the hair to perform a straightening function. The rearranging composition contains an aqueous solution of chemical agents capable of reducing the disulfide linkages in hair keratin. Suitable chemical agents include water soluble mercaptans, e.g. salts of thioglycolic acid, such as, sodium, monoethanolamine, or ammonium thioglycolate, and magnesium thioglycolate. Other sources of mercaptans include thioglycerol, sodium or potassium borohydride, and sodium or ammonium sulfite. The amount of these chemical agents may vary depending on, among other things, the degree of straightening desired, hair treatment history, and the chemical nature of the particular hair to be treated.

A preferred rearranging composition comprises a mixture of ammonium thioglycolate and monoethanolamine thioglycolate (MEA-Thio). However, it is within the scope of the invention that either thioglycolate compound may be used alone or as a substitute for the other. When a mixture of the two is used the ammonium thioglycolate is preferably present in concentration ranges of about 6.0 to about 10.0% by weight, and about 3.0 to about 7.0% by weight of the total rearranging composition. The MEA-Thio is preferably present in concentrations of about a most preferred rearranging composition comprises about 8.0% by weight of ammonium thioglycolate and about 5.5% by weight MEA thio. Alternatively, the rearranging composition may be characterized by the weight ratio of ammonium thioglycolate to MEA-Thio. A preferred ratio is between about 4:6 and about 7:3 ammonium thioglycolate to MEA-Thio, with a most preferred ratio of 6:4. When only one salt of the thioglycolic acid is used, the preferred concentration is between about 5.0 and 20% by weight. Additionally, a variety of conventional additives may be present in the rearranging composition, such as, conditioners perfumes, emollients, etc. The pH of the composition is adjusted to between 8.0 and 10.5, preferably using ammonium hydroxide.

Surprisingly and unexpectedly it has been found that the addition of a polyquaternary amine salt to the rearranging composition has a significant affect on the quality and settability of the hair both during and long after the waving process. The preferred polyquaternary amine salt is a highly charge cationic homopolymer of methacrylamidopropyltrimethyl ammonium chloride (MAPTAC). A preferred concentration of MAPTAC is from between about 1.0 to about 3.0% by weight of the rearranging composition, with a most preferred concentration of about 2.0% by weight. The average molecular weight of the MAPTAC homopolymer ranges from about 100,000 to about 200,000.

Although not completely understood it is believed that the MAPTAC increases the longevity of the curl pattern and the humectant qualities of the hair by penetrating into the pore of the hair. When the neutralizer solution is applied the polymer is believed to become "locked" into the hair. The increased integrity of the hair and the curl pattern that results from the application of MAPTAC greatly reduces the need for maintenance between subsequent waving treatments.

Additionally, a variety of conventional additives may be present in the rearranging composition, such as, conditioners, perfumes, moisturizers, emollients, etc. The pH of the composition is adjusted to between 8.0 and 10.5 using, preferably, ammonium hydroxide.

The rearranging composition is initially applied to the head and worked into the hair with gentle massage. The rearranging composition is allowed to stand, on the hair for about 5–15 or 20 minutes while the cystine bonds are being broken down to lanthonine bonds, the length of time the rearranger is allowed to stand depends upon the degree of curl in the hair's natural state and the degree of straightness desired.

After the hair has straightened to the desired degree, the hair is rinsed, preferably with warm water for about 3–5 minutes to flush away the major portion, preferably all, of the rearranging composition. In this way, the rearranging composition and the wrapping lotion composition are not applied to the hair at the same time.

After the hair has been rinsed, a wrapping lotion is applied to the head and gently massaged into the hair. The hair is then wrapped on rods, curlers, rollers or any other means known to the art to produce or establish a desired curl pattern. The wrapped hair containing the wrapping lotion is allowed to stand for a period of about 5–15 minutes, while the pattern of the curl becomes set.

The wrapping lotion of the invention is a homogeneous mixture including a salt of thioglycolic acid and a guar component. The wrapping lotion is specifically formulated to reduce the possiblity of oxidation of the hair that may occur due to air exposure. Thus, the wrapping lotion includes a reducing compound, as does the rearranger, but the reducing compound in the wrapping lotion is present in lower concentrations then in the rearranger. Oxidation is undesirable because it has the tendency to reverse the relaxing process which resulted from contact with the rearranging composition, and, thus, reform the cystine bonds prematurely.

The preferred salt of thioglycolic acid used in the wrapping lotion is ammonium thioglycolate. A preferred concentration range of the ammonium thioglycolate is between about 0.3 and 7.0% by weight of the total wrapping lotion composition, with a most preferred concentration of about 2% by weight. It is also within the scope of the invention that the wrapping lotion does not contain any appreciable amount of salt of thioglycolic acid, although some level of reducing agent is preferable as noted.

The guar component of the wrapping lotion is obtained from guar gum, also known as guar flower. Guar gum is a commercially available water soluble plant mucilage consisting of linear chains of galactose and manose molecules. A preferred source of guar is nonionic guar, most preferably a highly substituted hydroxypropylated guar gum.

Guar gum is a recognized thickening agent in systems that were not chemically active. However, it has now been discovered that guar gum can be used in a chemically active system, i.e., a system containing substantial amounts of active thioglycolates. Moreover, it has been discovered that the presence of the guar component in this wrapping solution significantly increases the volume and body of the hair as a result of the waving process. The curl pattern that results from the waving process is an overall more open/looser and bouncier pattern than was previously possible with prior art waving processes. Although the mechanism of the invention is not completely understood, it is believed that the use of a guar component in the wrapping lotion composition is directly attributable to producing the desired softer, bouncier more versatile curls. The guar component penetrates the hair where it is believed that the guar influences the reformation of the cystine bonds in the hair, so that when the neutralizer is applied the desired curl pattern is achieved. These advantages of using guar gum were unforeseen. A preferred concentration of the guar component in the wrapping lotion is from about 0.2 to about 2.5% by weight of the total composition, with a most preferred concentration of about 0.8% by weight.

In addition to the above components, the wrapping lotion composition may also contain other ingredients well known to the art, such as, emollients, conditioners, perfume, surfactants, moisturizers, etc. The wrapping lotion composition may be prepared by any suitable procedure known to the art. A preferred procedure involves first dissolving the guar component into water that is at or below ambient temperature. The water-guar solution is then heated to about 70°. Any additional ingredients are then added and the resulting mixture is cooled to about 50° F. Lastly, the salt of thioglycolic acid is added, if any, with an amount of ammonium hydroxide to adjust the pH of the final wrapping lotion composition to between about 7.0 to about 10.5, most preferably 9.0 to about 9.6. The resultant wrapping lotion composition has a gel consistency, with a viscosity range from about 500 cps to about 12,000 cps, most preferably from about 1,800 to about 2,200 cps.

After the wrapping lotion has been allowed to stand on the wrapped hair for a period of about 5 to about 15 minutes, the wrapped hair is then rinsed with warm water to remove any excess wrapping lotion composition.

After rinsing, a neutralizer is applied to the wrapped hair to restore the disulfide linkages in the hair keratin. The neutralizer "locks in" the curl pattern that was formed in the previous steps of the waving process. The exact composition of the neutralizer is not believed critical to achieve the improved results obtained by the waving process of the invention. As known to the art, neutralizers are typically aqueous solutions containing oxidizing agents, such as, sodium bromate. Other ingredients may be added to the neutralizer composition to improve the aesthetic properties of the hair. In particular, it has been found that the addition of from about 1.0 to about 5.0% by weight of ethoxylated castor oil greatly improves the sheen quality of the hair.

After application of the neutralizer, the wrapped hair is then rinsed with warm water to remove a substantial portion, preferably all, of the neutralizer composition. The rods are then removed and the hair is again rinsed with water. As an optional post-treatment step a sealer may be applied to the hair to elevate the initial dryness that sometimes results immediately after the hair has undergone a waving process. Well known to the art, sealers contain conditioners and humectants.

In order to more fully demonstrate the attendant advantages arising from the present invention, the following examples are set forth. It is to be understood that the following is by way of example of only and is not intended as an undue limitation on the otherwise broad scope of the invention.

EXAMPLE I

A waving process in accordance with the invention was performed using both an improved rearranging composition and an improved wrapping lotion. The first step in the process involved pre-shampooing the head with a suitable conditioning shampoo. The hair was then towel blotted dry. The improved rearranging composition was then applied to the hair by a tint-brush procedure in an effect to minimize scalp irritation. The rearranger used comprised a homogenous mixture of a homopolymer of MAPTAC and MEA thioglycolate. Table I lists the relative weight fractions of the rearranger components. The rearranger was allowed to stand on the hair for about 10 to 15 minutes until straight.

After the processing with the rearranger was completed the hair was rinsed thoroughly for about 3 to 5 minutes with warm water, then towel blotted dry. The improved wrapping lotion composition of the invention was then applied in ¼ head sections. The wrapping lotion comprised a homogenous mixture of ammonium thioglycolate and nonionic guar. Table II lists the relative weight fractions of the components for the improved rearranger. The hair in each ¼ section was then wrapped on rods to produce a curl pattern. After rodding, the wrapping lotion was allowed to stand on the hair for about 10 minutes.

The hair with the rods intact was then rinsed thoroughly with warm water and then towel blotted dry.

A conventional neutralizer solution having sodium bromate as the active ingredient was then applied sparingly to each rodded portion of hair and allowed to stand for about 10 minutes under a plastic wrap. After processing with the neutralizer, the rodded hair was then rinsed well with warm water for about 3 to 5 minutes to substantially remove the neutralizer. The hair was then unrodded, rinsed again, and dried under a conventional hair dryer.

The resultant hair style obtained from the waving process of the instant invention was characterized as having a looser, bouncier, more open pattern of curls than hair styles previously possible using prior art waving process. The hair resulting from the Example I was characterized as having thicker, more full bodied hair than results from prior art waving processes. In addition, the longevity of the curl pattern produced and the humectant quality of the hair was increased on a relatively long term basis with substantially lower need for application of maintenance products. The softer, bouncier curls obtained as a result of the instant process is believed directly attributable to the use of the improved wrapping lotion composition, containing the guar component.

EXAMPLE II

For the purposes of comparison to the improved waving process of the invention as described in Example I, a conventional prior art waving process was performed. The procedure use for the conventional waving process was identical to that of the waving process of Example I with the exception that the wrapping lotion used did not contain a guar component, and the rearranger did not contain a homopolymer of MAPTAC. Also, ammonium thioglycolate was substituted for MEA thioglycolate. The wrapping lotion and rearranger formulations detailed in Tables I and II.

The resultant hair style obtained from the conventional waving process was characterized as relatively tightly curled, dry, and frizzy in appearance. Furthermore, this style required the application of maintenance products, such as, moisturizers and curl activators. These maintenance products cause an overall greasy look of the hair style.

TABLE I

| | | |
|---|---|---|
| Deionized H$_2$O | 59.7 | 59.6 |
| MAPTAC | 2.0 | — |
| Ammonium Thioglycolate | 8.0 | 10.0 |
| MEA Thioglycolate | 5.5 | — |
| Other Ingredients[1] | 24.8 | 30.4 |

[1]Conditioners, surfactants, pH adjusters, moisturizers and fragrance.

TABLE II

| | Example I | Example II |
|---|---|---|
| Deionized H$_2$O | 92.6 | 92.6 |
| Ammonium Thioglycolate (60% solution) | 2.0 | 2.0 |
| Nonionic Guar | 0.75 | — |
| Other ingredients | balance | balance |
| pH | 9.1–9.3 | 9.1–9.3 |
| Viscosity, cps | 1,800–2,200 | 1,200–1,600 |
| Appearance | gel/lotion | lotion |

The foregoing examples and specification disclose preferred and generalized illustrations of the invention. However, variations are possible within the scope of the invention. For example, the wave wrapping lotion of this invention is believed to provide advantages when used with any rearranger or neutralizer. It should be understood, therefore, that the invention is to be limited only by the following claims and their equivalents.

What is claimed:

1. A process for waving hair, comprising the following steps in combination:
   (a) applying to the hair a rearranging composition with chemical properties sufficient to break the cystine bonds in the hair keratin, said rearranging composition comprises a homogeneous mixture of a salt of thioglycolic acid and a cationic homopolymer of methylacrylamidopropyltrimethyl ammonium chloride;
   (b) rinsing the hair to substantially remove the rearranging composition;
   (c) applying a wrapping lotion composition to the hair, said wrapping lotion comprises a homogeneous mixture which includes a salt of thioglycolic acid and a guar component;
   (d) wrapping the hair around a rod to produce a curl pattern and allowing the hair and wrapping lotion to set for a predetermined length of time;
   (e) rinsing the wrapped hair;
   (f) applying a neutralizer composition to the curl pattern; and
   (g) rinsing the hair to substantially remove the neutralizer composition, whereby the process produces thicker, fuller hair with loose, bouncy curls.

2. The process of claim 1 wherein the wrapping lotion composition comprises:
   (a) between about 0.2 and about 2.5% by weight of a guar component; and
   (b) between about 0.0 and about 7.0% by weight of a salt of thioglycolic acid.

3. The process of claim 2 wherein the wrapping lotion composition has a pH of between 7.0 and 10.5.

4. The process of claim 2 wherein the guar component comprises a nonionic guar.

5. The process of claim 4 wherein the nonionic guar comprises a highly substituted hydroxypropylated guar.

6. The process of claim 2 wherein the salt of thioglycolic acid of the wrapping lotion comprises ammonium thioglycolate.

7. The process of claim 2 wherein the wrapping lotion composition has a viscosity of from about 1,800 to about 2,200 cps.

8. The process of claim 1 wherein the rearranging composition comprises:
   (a) between about 5.0 and about 20% by weight of a salt of thioglycolic acid; and
   (b) between about 1.0 and about 3.0% by weight of a cationic homopolymer of methylacrylamidopropyltrimethyl ammonium chloride.

9. The process of claim 8 wherein the salt of thioglycolic acid of the rearranging composition comprises ammonium thioglycolate.

10. The process of claim 8 wherein the salt of thioglycolic acid of the rearranging composition comprises monoethanolamine thioglycolate.

11. The process of claim 8 wherein the salt of thioglycolic acid of the rearranging composition comprises a mixture of ammonium thioglycolate and monoethanolamine thioglycolate.

12. The process of claim 11 wherein the weight ratio of ammonium thioglycolate to monethanolamine thioglycolate is between about 4:6 and about 7:3.

13. A process of claim 8 wherein the rearranging composition is at a pH of between 8.0 and about 10.5.

14. A process for waving hair, comprising the following steps in combination:
   (a) applying to the hair a rearranging composition with chemical properties sufficient to break the cystine bonds in the hair keratin, said rearranging composition comprises between about 6.0 and about 10.0% by weight ammonium thioglycolate, between about 5.0 and about 7.0% by weight monoethanolamine thioglycolate, and between about 1.0 and about 3.0% by weight of a cationic homopolymer of methylacrylamidopropyltrimethyl ammonium chloride;
   (b) rinsing the hair to substantially remove the rearranging composition;
   (c) applying a wrapping lotion composition to the hair, said wrapping lotion comprises between about 0.2 and about 2.5% by weight of nonionic hydroxypropylated guar and between about 0.3 and about 7.0% by weight of ammonium thioglycolate;
   (d) wrapping the hair around a rod to produce a curl pattern and allowing the hair and wrapping lotion to set for a predetermined length of time;
   (e) rinsing the wrapped hair;
   (f) applying a neutralizer composition to lock in the curl pattern; and
   (g) rinsing the hair to substantially remove the neutralizer composition, whereby the process produces thicker, fuller hair with loose, bouncy curls.

* * * * *